United States Patent

Agbossou et al.

[11] Patent Number: 6,118,025
[45] Date of Patent: Sep. 12, 2000

[54] METHOD FOR PREPARING OPTICALLY ACTIVE α-SUBSTITUTED BENZYL ALCOHOLS

[75] Inventors: Francine Agbossou, Libercourt; Marc Devocelle, Lille; Jean-Robert Dormoy, Sisteron; André Mortreux, Hem, all of France

[73] Assignee: Sanofi-Synthelabo, Paris, France

[21] Appl. No.: 09/254,218

[22] PCT Filed: Sep. 10, 1997

[86] PCT No.: PCT/FR97/01592

§ 371 Date: Dec. 27, 1999

§ 102(e) Date: Dec. 27, 1999

[30] Foreign Application Priority Data

Sep. 11, 1996 [FR] France ................................ 96 11065

[51] Int. Cl.[7] .................................................. C07B 57/00
[52] U.S. Cl. .......................... 564/304; 564/424; 564/442; 564/437
[58] Field of Search .......................... 564/304, 424, 564/442, 437

[56] References Cited

U.S. PATENT DOCUMENTS 5,128,488 7/1992 Mortreux et al. .

FOREIGN PATENT DOCUMENTS 0 443 923 8/1991 European Pat. Off. .

OTHER PUBLICATIONS

T. Hayashi et al., "Asymmetric Synthesis of 2–Amino–1–Arylethanols by Catalytic Asymmetric Hydrogenation", *Tetrahedron Letters*, 1979, 5, 425–428.

M. Nogradi, "Stereoselective Synthesis", *VCH* (Weinheim DE), 1987, pp. 53–89, XP0020208705, 89.

A. Roucoux et al., "Amidophosphine–Phosphinites: Synthesis and Use in Rhodium–Based Asymmetric Hydrogenation of Activated Keto Compounds . . . ", *Organometallics*, 1996, 15, 2440–2449.

A. Roucoux et al., "Highly Efficient Asymmetric Hydrogenation of Activated and Unactivated Ketones Catalyzed by Rhodium(I) Aminophosphine . . . ", *Synlett*, Apr. 1995, 358–360.

Primary Examiner—Samuel Barts
Attorney, Agent, or Firm—Michael D. Alexander

[57] ABSTRACT

The invention concerns a method for preparing an optically active alcohol of formula (I)

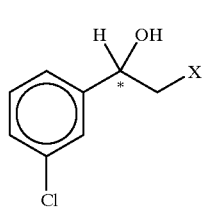

(I)

in which the carbon atom indicated by the symbol * can have the configuration (R) or (S) and X represents a non-substituted amino group or a mono- or di-($C_1$–$C_4$) alkylamino group optionally salified from corresponding ketones by catalytic hydrogenation in the presence of a rhodium complex.

14 Claims, No Drawings

METHOD FOR PREPARING OPTICALLY ACTIVE α-SUBSTITUTED BENZYL ALCOHOLS

The present invention relates to a method for preparing optically active α-substituted benzyl alcohols from the corresponding ketones.

The optically active α-substituted benzyl alcohols are key intermediates in the synthesis of numerous pharmaceutical products, especially in the preparation of phenylethanolamines active on β-adrenergic receptors.

One of the synthetic approaches for these products is the asymmetric reduction of ketones with the aid of chiral catalysts. Such chiral catalysts are, for example, described in Organometallics, 15: 24401–2449, 1996; in Synlett, April 1995, 358–360; in EP-A-0 253 700 and in EP-A-0 443 923.

These documents describe classes of Group VIII metal complexes, especially rhodium complexes, which contain, inter alia, chiral ligands; more particularly, these documents describe complexes wherein the components are bound to the metal atom via "covalent" bonds.

It has now been discovered that "ionic"-type rhodium complexes are very efficient catalysts in the preparation of optically active α-substituted benzyl alcohols.

Thus, the present invention relates to a method of preparing an optically active alcohol of formula (I):

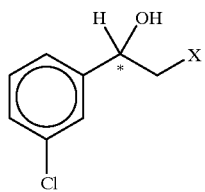
(I)

in which the carbon atom indicated by the symbol * can have the (R) or (S) configuration and X represents a non-substituted amino group or a mono- or di-($C_1$–$C_4$) alkylamino group, which are optionally salified, characterised in that:

a/ a ketone of formula (II):

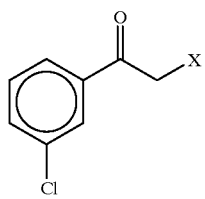
(II)

in which X is as defined above, is subjected to a catalytic hydrogenation in the presence of a rhodium complex of formula (III):

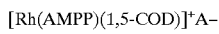
[Rh(AMPP)(1,5-COD)]⁺A⁻  (III)

in which (AMPP) represents a chiral aminophosphinephosphinite of formula (IV):

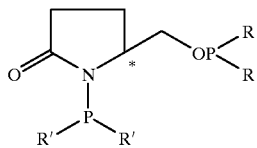
(IV)

wherein the carbon atom indicated by the symbol * can have the (R) or (S) configuration, R and R' represent a cyclohexyl or a cyclopentyl, (1,5-COD) represents 1,5 cyclooctadiene and A represents a sterically hindered and little-coordinating monovalent anion; and b/ the optically active alcohol of formula (I) is isolated.

The term "($C_1$–$C_4$)alkyl" designates a linear or branched alkyl residue containing 1 to 4 carbon atoms, such as methyl, ethyl, n-propyl, i-propyl, n-butyl, i-butyl, s-butyl and t-butyl.

The term "sterically hindered and little-coordinating monovalent monovalent anion" according to the present invention designates an anion such as perchlorate, tetrafluoroborate, tetraphenylborate or hexafluorophosphate. A particularly preferred anion is tetrafluoroborate.

The non-substituted amino groups or mono- or di-($C_1$–$C_4$)-alkylamino groups can be salified for example with a molecule of hydrochloric acid.

According to a preferred aspect, the present invention relates to a method for preparing an optically active alcohol of formula (I'):

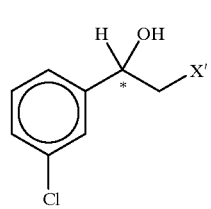
(I')

in which X' represents a non-substituted amino group or dimethylamino group, which are salified with a molecule of hydrochloric acid, characterised in that:

a/ a ketone of formula (II'):

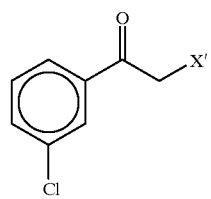
(II')

in which X' is as defined above, is subjected to a catalytic hydrogenation in the presence of a rhodium complex of formula (III'):

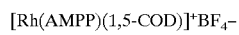
[Rh(AMPP)(1,5-COD)]⁺BF₄⁻  (III')

in which (AMPP) is as defined above; and b/ the optically active alcohol of formula (I') is isolated.

The absolute configuration of the alcohols of formula (I) is determined by the configuration of the aminophosphine-phosphinite which is used. When an aminophosphinephosphinite of (S) configuration is used, the alcohols of (S) configuration are obtained selectively, and when an aminophosphine-phosphinite of (R) configuration is employed, the alcohols of (R) configuration are obtained.

The asymmetric hydrogenation according to the present invention is conducted in a protic solvent such as, for example, an alcohol, such as methanol or ethanol.

The reaction temperature is generally between −30° C. and the reflux of the reaction solvent, preferably between 20° C. and 50° C.

The hydrogenation of the present invention can be carried out at atmospheric pressure or under pressure; advantageously, the reaction is conducted at a pressure of hydrogen between 1 and 80 bar, especially between 20 and 50 bar.

The amount of catalyst to be used is between 0.005 and 2% by mole with respect to the starting ketone, preferably between 0.1 and 1%, advantageously about 0.5%.

The reaction times, even if they vary as a function of other parameters of the reaction, are very short; in general, a period of time of a few hours is sufficient for a 100% conversion of the starting product.

The alcohols of formulae (I) and (I') are isolated according to usual techniques, for example by evaporation of the solvent after filtering the catalyst off.

The "ionic" catalysts of formula (III), especially those of formula (III'), are in fact more efficient than the "covalent" catalysts used according to EP-A-0 443 923 and in Synlett, April 1995, 358–360, in the asymmetric reduction of the present invention. More particularly, the use of the catalysts of formula (III) and especially of formula (III') according to the present invention enable reducing the reaction time enormously; an element which, above all in working at an industrial level, constitutes an significant advantage.

The starting ketones of formula (II) are known compounds.

The catalysts of formula (III) and especially of formula (III') are prepared as described in EP-A-0 443 923 and in Synlett, April 1995, 358–360.

The method of the present invention enables obtaining practically pure enantiomeric forms of the alcohols of formula (I), said enantiomeric forms having in general an enantiomeric excess of greater than 95%.

The very pure alcohols of formula (I) thus obtained can therefore be used as starting products for the preparation of phenylethanolamines having β-adrenergic action, for example the alcohols of formula (I) of (R) configuration are useful in the synthesis of the ethyl ester of {(7S)-7-[(2R)-2-(3-chlorophenyl)-2-hydroxyethyl-amino]-5,6,7,8-tetrahydronaphthalen-2-yloxy}acetoc acid, a compound which is under study for its β₃-adrenergic receptor agonist activity.

The Examples that follow illustrate the invention.
Method

The hydrochloride of the ketone of formula (II) is dissolved in methanol. The solution is introduced into an autoclave and is placed under nitrogen. The catalyst of formula (III) is dissolved in methanol and is transferred, under nitrogen, into the autoclave with the aid of a cannula. The autoclave is placed under vacuum and then under a pressure of hydrogen (50 bar), followed by a de-pressurisation down to 3–5 bar. The operation is repeated twice before placing under definitive hydrogen pressure. Stirring is commenced and the reaction is left to take place. After de-pressurisation of the autoclave, the solvent is evaporated off from the crude reaction mixture. The reaction product is extracted by treating the solid with 10 ml of water.

The catalyst is filtered off on a sinter, ethanol is added to the filtrate to facilitate the evaporation of water, and the solvent is evaporated off under reduced pressure. The compound of formula (I) is obtained. Table I shows the results of Examples 1 to 3. The determination of the enantiomeric excess of the alcohol of formula (I), wherein X is a non-substituted amino group, is conducted on the N-benzoyl derivative which is prepared from a sample of the product according to the following method: 78.6 mg (0.4 mmol) of amino compound is stirred at ambient temperature for 2.5 hours with 53.1 mg (0.4 mmol) of benzoyl chloride and 84 mg (2.2 mmol) of triethylamine in 10 ml of tetrahydrofuran. The triethylamine hydrochloride is removed by filtration and the residue is evaporated on a rotary evaporator. A white solid is obtained.

TABLE I

| Ex | ketone of formula (II) | AMPP of formula (IV) (S) isomer | reaction conditions bar H₂ | temp. ° C. | time h. | conversion | yield | alcohol of formula (I) (S) isomer e.e. |
|---|---|---|---|---|---|---|---|---|
| 1 | X = —NMe₂·HCl | R = R' = cyclopentyl | 50 | 20 | 2 | 100% | 83% | 96% * |
| 2 | X = —NMe₂·HCl | R = R' = cyclohexyl | 50 | 20 | 2 | 98% | 86% | 96%* |
| 3 | X = —NH₃Cl | R = R' = cyclopentyl | 50 | 20 | 1.5 | 100% | 80% | 95% ** |

The enantiomeric excesses are evaluated by HPLC on a Chiralcel OD column (Daicel):
* elution: isopropyl alcohol/hexane: 5/95; 0.4 ml/min (free base).
** elution: isopropyl alcohol/hexane: 10/90; 0.6 ml/min (N-benzoyl product).

What is claimed is:

1. A method of preparing an optically active alcohol of formula (I):

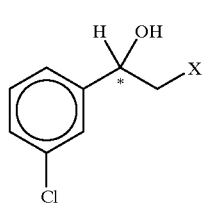

(I)

in which the carbon atom indicated by the symbol * can have the (R) or (S) configuration and X represents a non-substituted amino group or a mono- or di-($C_1$–$C_4$) alkylamino group, which are optionally salified, wherein:
a/ a ketone of formula (II):

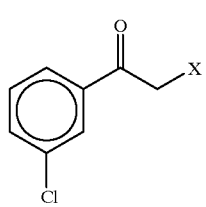

(II)

in which X is as defined above, is subjected to a catalytic hydrogenation in the presence of a rhodium complex of formula (III):

[Rh(AMPP)(1,5COD)]⁺A⁻   (III)

in which (AMPP) represents a chiral aminophosphine-phosphinite of formula (IV):

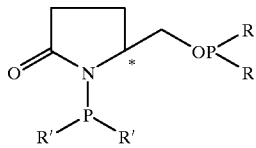

(IV)

wherein the carbon atom indicated by the symbol * can have the (R) or (S) configuration, R and R' independently represent a cyclohexyl or a cyclopentyl and (1,5-COD) represents 1,5-cyclooctadiene and A⁻ represents a sterically hindered and little-co-ordinating monovalent anion; and b/ the optically active alcohol of formula (I) is isolated.

2. The method according to claim 1 for preparing an optically active alcohol of formula (I'):

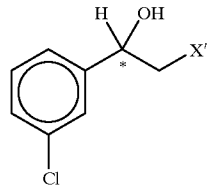

(I')

in which X' represents a non-substituted amino group or a dimethylamino group, which are salified with a molecule of hydrochloric acid, wherein:

a/ a ketone of formula (II'):

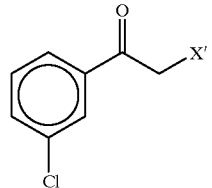

(II')

in which X' is as defined above, is subjected to a catalytic hydrogenation in the presence of a rhodium complex of formula (III'):

[Rh(AMPP)(1,5-COD)]⁺BF₄⁻   (III')

in which (AMPP) is as defined above; and b/ the optically active alcohol of formula (I') is isolated.

3. The method according to claim 1 wherein an aminophosphine-phosphinite of (S) configuration is used to give the alcohol of formula (I) of (S) configuration.

4. The method according to claim 1 wherein an aminophosphine-phosphinite of (R) configuration is used to give the alcohol of formula (I) of (R) configuration.

5. The method according to claim 1 wherein the reaction temperature is between −30° C. and the reflux temperature of the solvent.

6. The method according to claim 1 wherein the reaction temperature is between 20° C. and 50° C.

7. The method according to claim 1 wherein the reaction is conducted under a pressure of hydrogen between 1 and 80 bar.

8. The method according to claim 1 wherein the amount of catalyst is between 0.005 and 2% by mole with respect to the starting ketone.

9. The method according to claim 1 wherein X is a dimethylamino group salified with a molecule of hydrochloric acid.

10. The method according to claim 1 wherein X is a non-substituted amino group salified with a molecule of hydrochloric acid.

11. The method according to claim 2 wherein an aminophosphine-phosphinite of (S) configuration is used to give the alcohol of formula (I') of (S) configuration.

12. The method according to claim 2 wherein an aminophosphine-phosphinite of (R) configuration is used to give the alcohol of formula (I') of (R) configuration.

13. The method according to claim 1 wherein the amount of catalyst is between 0.1 and 1% by mole with respect to the starting ketone.

14. The method according to claim 1 wherein the amount of catalyst is about 0.5% by mole with respect to the starting ketone.

* * * * *